United States Patent [19]

Mount et al.

[11] Patent Number: 4,955,946
[45] Date of Patent: Sep. 11, 1990

[54] RESPIRATORY $CO_2$ DETECTOR CIRCUIT WITH HIGH QUALITY WAVEFORM

[75] Inventors: Bruce E. Mount, Diamond Bar; Douglas P. Becker, Walnut, both of Calif.

[73] Assignee: Marquette Gas Analysis, St. Louis, Mo.

[21] Appl. No.: 306,234

[22] Filed: Feb. 2, 1989

Related U.S. Application Data

[63] Continuation of Ser. No. 939,992, Dec. 11, 1986, abandoned.

[51] Int. Cl.$^5$ .............................................. A61B 5/087
[52] U.S. Cl. ...................................... 128/719; 128/725
[58] Field of Search ...................... 128/716, 719, 725

[56] References Cited

U.S. PATENT DOCUMENTS

| | | | |
|---|---|---|---|
| 4,011,859 | 3/1977 | Frankenberger | 128/719 |
| 4,368,740 | 1/1983 | Binder | 128/719 |
| 4,423,739 | 1/1984 | Passaro et al. | 128/633 |
| 4,578,762 | 3/1986 | Wong | 128/719 |
| 4,648,396 | 3/1987 | Raemer | 128/204.22 |

Primary Examiner—Lee S. Cohen
Assistant Examiner—John C. Hanley
Attorney, Agent, or Firm—Gerald M. Newman

[57] ABSTRACT

A respiratory $CO_2$ detector (10) comprising an infrared lamp source (44) and an infrared detector (50) responsive thereto forming an optical path for detecting the change in $CO_2$ concentration, or an obstruction in a cuvette (42). The output of the infrared detector (50) provides a high and low voltage signal to be applied to a feedback control loop (12) and to an output circuit (14).

The feedback control loop (12) includes a peak detector (22), a contamination detector (24), a pulse-width modulator (26) and a low pass filter (28), the latter providing a DC bias on the infrared lamp (44). The peak detector (22) is connected to the pulse-width modulator (26) to maintain the lamp voltage constant and is connected to comparators (56,62) to compare both outputs of the peak and contamination detectors (22,24). The contamination detector (24) will respond to blockage in the cuvette (42).

The output control circuit (14) includes a sample-and-hold circuit (30) and a subtractor (32) connected to the output of said infrared detector to receive the high and low voltage signal from the infrared detector, the outputs of which produce an output signal without the DC bias which is then inverted to provide a high quality waveform.

7 Claims, 1 Drawing Sheet

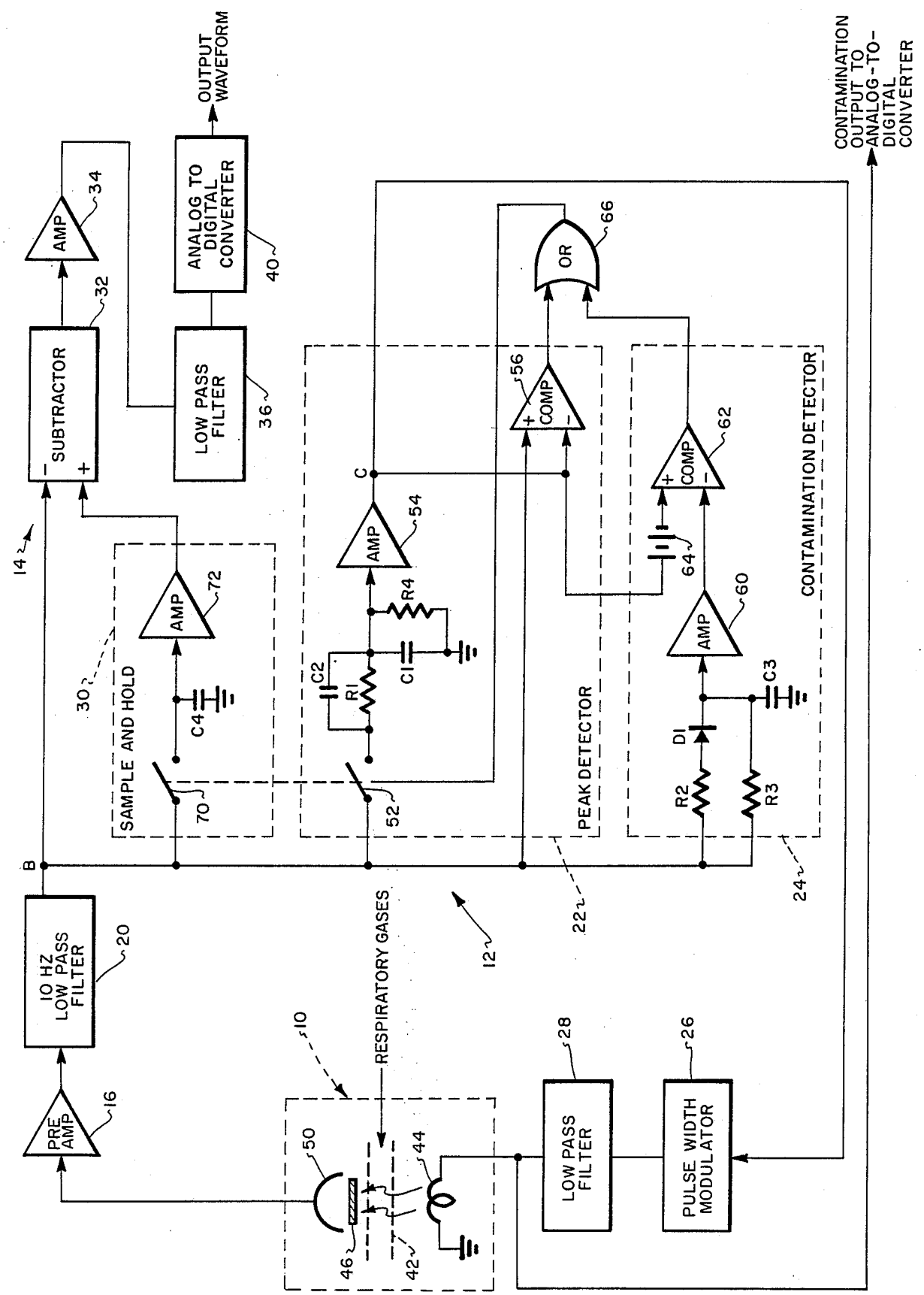

RESPIRATORY CO₂ DETECTOR CIRCUIT WITH HIGH QUALITY WAVEFORM

This is a continuation of application Ser. No. 939,992, filed Dec. 11, 1986, now abandoned.

BACKGROUND OF THE INVENTION

This invention relates to $CO_2$ detectors for use as part of a respiratory breath monitoring system for patients, usually in a hospital environment, and is specifically directed to a respiratory $CO_2$ detector circuit which produces a high quality waveform from a cuvette for diagnostic purposes.

Still more specifically, this invention is an improvement over a respiratory $CO_2$ detector disclosed by D. Raemer in a U.S. Pat. application Ser. No. 730,158, entitled "Respiration Detector" filed May 3, 1985, now U.S. Pat. No. 4,648,369.

The Raemer patent application disclosed a respiratory $CO_2$ detector which included a sensor with a cuvette, a lamp as an infrared source, an infrared detector and amplifier for detecting the quantity of $CO_2$ gas in the cuvette, and suitable electronic amplification circuitry. In this system, an increase concentration of $CO_2$ gas in the cuvette resulted in an increased amount of energy absorption and less output from the infrared detector. A waveform of $CO_2$ gas in the cuvette looks similar to a square wave. The high peaks represent approximately 5% concentration on exhalation and the valleys represent zero percent concentration on inhalation. The resulting detector output should closely approximate the inverse of the $CO_2$ gas waveform, however, due to reasons to be described, the actual waveform was greatly distorted. Power for the infrared source was adjusted in the circuitry automatically depending upon the amount of attenuation in the optical path.

In this prior art scheme, no chopper or other reference was employed in order to keep manufacturing costs low. No attempt was made to preserve the quality of the $CO_2$ output waveform because only an alarm signal level was desired to indicate low $CO_2$ for the detection of apnea. Since no reference was employed, an artificial reference was developed by sensing the minimum $CO_2$ concentration from each breath and controlling the lamp voltage to maintain a constant voltage output from the detector amplifier. Thus, more lamp voltage was applied when the optical path was attenuated due to water vapor and/or particulate contamination from the gas sample which tended to maintain the output voltage sensitivity to $CO_2$ concentration in the dynamic breath waveform constant. The quality of the breath waveform was degraded because the system was designed to follow slow changes in $CO_2$ concentration and slow changes in optical path contamination. This caused a "droop" in the $CO_2$ waveform which was especially noticeable at lower breath rates of approximately four to six breaths per minute. In order to refer the waveform generated by the Baemen instrument to a baseline-suitable for reliable operation of a threshold detector, the waveform was connected to a high pass filter, which caused further distortion. This rendered the output waveform useless for diagnostic purposes. Nonetheless, the Raemer instrument did accomplish the purposes intended which were to (1) indicate by a flashing light when each expiratory breath occurred, and (2) sound an alarm when expiratory breaths were not present for a predetermined time.

When monitoring the concentration of $CO_2$ in a patient's expired respiratory breath, it is important to have a high quality output waveform for diagnostic purposes.

This invention maintains the advantage of low manufacturing cost made possible by the Raemer invention, but enables the high quality $CO_2$ waveform to be obtained for diagnostic purposes.

Therefore, an object of this invention is to provide a respiratory $CO_2$ detector with
  (1) a high quality waveform without additional requirements for references for zero $CO_2$ or full scale $CO_2$,
  (2) a high quality waveform in which the minimum $CO_2$ concentration is referred to a stable zero baseline,
  (3) the ability to follow slow changes in $CO_2$ concentration with minimal waveform distortion.
  (4) the ability to compensate for slow changes in optical path transmission with minimal waveform distortion.

SUMMARY OF THE INVENTION

The respiratory $CO_2$ detector which meets the foregoing object comprises an infrared lamp source and an infrared detector responsive thereto forming an optical path for detecting the presence or absence of $CO_2$, or, an obstruction in a cuvette. The output of the infrared detector provides a voltage signal which is applied to a feedback control loop and to an output circuit.

The feedback control loop includes a preamplifier, a lowpass filter, a peak detector, a contamination detector and a pulse-width modulator, the latter providing a DC bias on the infrared lamp. The output of the peak detector is connected to the pulse-width modulator to maintain the lamp voltage constant and to comparators, one of which is necessary for operation of the peak detector, and the other is part of the contamination detector. The contamination detector will respond to blockage in the cuvette by readjusting the feedback loop to a normal condition.

The output control circuit includes a sample-and-hold circuit activated by the peak detector to direct the high and low voltage signal to a subtractor where the bias from the preamplifier output is eliminated. The output of the subtractor is then inverted to provide a high quality output waveform representative of the concentration of the $CO_2$ gas in the cuvette.

BRIEF DESCRIPTION OF THE DRAWINGS

The sole FIGURE is a block diagram of the respiratory $CO_2$ detector whose output is a high quality waveform useful for diagnostics.

DETAILED DESCRIPTION

Circuit Description

In The drawing it can be seen that the $CO_2$ detector circuit of this invention includes a sensor 10 connected to a feedback control loop 12 and to an output circuit 4.

The feedback control loop 12 includes a preamplifier 16, a low pass filter 20, a peak detector 22, a contamination detector 24 and a pulse-width modulator 26 and a second low pass filter 28.

The output circuit 14, which is connected to the output of the low pass filter 20 includes a sample-and-hold circuit 30, a subtractor 32, an amplifier 34, a low pass filter 36 and an analog-to-digital converter 40. The output of the latter is the high quality output waveform.

The sensor 10 comprises a cuvette 42, a lamp 44 defining an optical path by radiating infrared energy transversely through the cuvette, through an optical bandpass and onto an infrared $CO_2$ detector 50. The output of the lowpass filter 36 is the high quality waveform in analog form, while the analog digital converter is the digitized form of the waveform for acceptance by a microprocessor.

The output of the infrared detector 50 is connected to the preamplifier 16 whose output is connected to the low pass filter 20. The output of the low pass filter 20 is connected at point B to the peak detector 22, to the negative input of the subtractor 32, to the sample-and-hold circuit 30 and to the contamination detector 24

The peak detector 22 is connected at point B in two places. First, an analog switch 52 is connected to point B. This switch 52 connects an RC network comprising resistor R1, capacitors C1 and CZ and resistor R4. Capacitor C2 is connected in parallel with resistor R1 and capacitor C1 is connected in series with resistor R2 and to ground. Resistor R4 is also connected to ground and in parallel with capacitor C1. The output of the RC network is connected to a buffer amplifier 54 and the output of the latter is connected to one input (−) of a comparator 56 and to the pulse-width modulator 26. The output of the pulse-width modulator is connected to the second low pass filter 28.

The second connection of the peak detector 22 to point B is directly to the other input (+) of the comparator 56.

The contamination detector 24 is also connected to point B and comprises a second RC network comprising resistor R2, R3, diode D1, and capacitor C3. Resistor R3 is connected in series with the capacitor C3 and the latter is connected to ground. A second resistor R2 and diode D1 are connected in parallel with resistor R3 and the output of this network is connected to the input of an amplifier 60. The output of amplifier 60 is connected to one input (−) of a second comparator 62. The other input (+) of comparator 62 is connected to the other input (−) of comparator 56 through a negative bias 64. The output of both comparators are connected to an OR gate 66 whose output is connected back to the switch 52 and to switch 70 of the sample-and-hold circuit 30 to be responsive thereto.

The output circuit 14 is connected to the low pass filter 20 at point B in two places. First, the analog switch 70 of the sample-and-hold circuit 30 connects point B to one side of a capacitor C4 and to the input of amplifier 72. The other side of capacitor C4 is connected to ground. Switch 70 is ganged with switch 52 and both are responsive to the output of the OR gate 66. The output of amplifier 72 is connected to one input of the subtractor 32. The other input of the subtractor is connected directly to point B. Again, the output of the subtractor 32 is connected to an input of inverting amplifier 34. The output of amplifier 34 is connected to low pass filter 36 and analog-to-digital converter 40.

Circuit-Operation

Conventionally, the cuvette 42 is connected to a patient's breathing circuit to measure the $CO_2$ concentration of the expired breaths. A gas sample is drawn through the cuvette via a capillary tube from the cuvette to a vacuum source, and another capillary tube is connected from the cuvette to an adapter inserted in series with a conventional airway tube which is in turn connected from a respiratory ventilation device to the patient's airway. A typical respiratory $CO_2$ concentration waveform can be represented by a somewhat rounded square wave. The baseline (valley of the square wave) represents inhalation (typically 0% $CO_2$) and the peak of the waveform represents exhilation (typically 5% $CO_2$) by a patient.

The pulse-width modulator 26 has an internal reference voltage of +5 VDC which is internally compared to the voltage at point C (the output of amplifier 54) to maintain a DC level at point B. The low pass filter 28 provides DC voltage to lamp 44. The bandwidth of the optical bandpass filter 46 is optimized to be within the energy absorption band of $CO_2$ gas. The output voltage of the infrared detector 50 is proportional to the amount of radiation received from the lamp 44. This voltage decreases when $CO_2$ is present, or the optical path is obstructed such as by water droplets or particulate matter, and increases when the optical path is free of $CO_2$. Breathing, therefore, is represented at point "B" by an inverted (and offset) version of the actual $CO_2$ concentration waveform passing through the cuvette.

Thus, $CO_2$ gas in the cuvette is detected by the detector 50. The above-mentioned feedback control loop 12 is actually a gain control for the voltage at lamp 44 to keep the DC bias at print B constant.

When the percentage of $CO_2$ is zero, or when the optical path is not otherwise obstructed, the output voltage at point B is a positive voltage of approximately +4 VDC. This voltage is applied directly to the positive input of the comparator 56. The output of the comparator 56 is applied to the OR gate 66 which momentarily closes the switch 52. (This is the situation also when the circuit is originally placed in operation). The closing of this switch allows the DC voltage at point B to charge the capacitors C1 and C2 in the peak detector 22 to the minimum $CO_2$ concentration voltage (or maximum DC voltage). The switches open when the $CO_2$ concentration begins to increase above zero percent (voltage at point "B" decreases).

During the increase of the percentage of $CO_2$ to a peak the voltage at point B gradually drops to a low voltage. This drop in voltage is applied to the positive input of the comparator 56 which voltage level is less than the voltage at the negative input to this comparator 56 by reason of the fact that the RC network of the peak detector maintained a high voltage (with a slight gradual drop) at the output of the amplifier 54. This same voltage, being applied to the input of the pulse-width modulator 26, provides only a gradual decrease in voltage at the lamp 44.

When the $CO_2$ decreases with a consequent increase in voltage, this voltage increase is again applied to the comparator 56, momentarily closing the switch 52 and again charging the RC network as before.

This cyclical operation of the feedback control loop maintains the voltage on the lamp 44 and the DC reference at point B constant so that the waveform at point B is representative of the condition of the cuvette.

During the same cyclical operation, capacitor C4 in the sample-and-hold circuit 30 is charged when the switch 70 is closed and is allowed to discharge when the switch 70 is open. This provides an output signal at the positive input of the subtractor 32. Since the negative input of the subtractor 32 is connected directly to point B, the subtractor serves to subtract the DC bias at point B to provide a zero VDC baseline for the waveform.

Since this waveform is inverted, the output of the subtractor 32 is applied to the inverting amplifier 34, the output of which ultimately shows a high quality waveform referred to a zero baseline.

During the cyclical operation of the feedback control loop, the high and low voltages at point 8 are also applied to the RC network of the contamination detector 24. The capacitor C3 is charged during high voltage at point B and allowed to discharge during low voltage at point B and the output of the RC network is applied to amplifier 60 and then to the negative input of comparator 62. The positive input of comparator 62 is the output from amplifier 54 of the peak detector 22, less a negative DC bias 64. Therefore, when the DC output of the contamination detector amplifier 60 falls below the DC voltage at comparator 62 positive input, the output of the comparator 62 will switch from zero VDC to +12 VDC, causing switches 70 and 52 to close momentarily until capacitor C3 again charges to a higher DC voltage, bringing comparator 62 negative input more positive than the positive input. Since the discharge time constant of the RC network of the peak detector is many times longer than the discharge time constant of the RC network of the contamination detector 24, the function of the contamination detector 24 is muted until such time as the contamination in the cuvette causes the voltage at point B to remain lower than the output of the peak detector amplifier 54, minus a DC bias, for a period of time beyond the time constant of the contamination detector whereupon the contamination detector will close the switches 52 and 70 driving the voltage at the output of the peak detector amplifier 54 to a low level. At this time, the feedback loop automatically tries to increase the lamp voltage to maintain the voltage at point B at +4 volts. If the lamp voltage increases beyond a predetermined level due to excessive contamination, external processing circuitry can be employed to sound an alarm.

The peak detector RC network charge time constant is approximately 13 sec and the discharge time constant is approximately 20,000 sec. The contamination detector RC network charge time constant is a few milliseconds and the discharge time constant is approximately 100 sec. The system response time when blockage occurs in the cuvette is at least equal to or less than 30 sec.

It should be apparent that the high quality waveform of this invention can be analyzed by computer processing to provide alarms when the expired breath $CO_2$ concentration falls below a predetermined level, for example, 1% to 2%.

We claim:

1. A $CO_2$ detector for monitoring a patient's breath inhalation and exhalation directed through a cuvette, comprising, an infrared lamp having an input and responsive to a lamp voltage applied thereto, a circuit including a pulse-width modulator and a lowpass filter connected to said lamp input to provide said lamp input voltage, an infrared detector, a preamplifier having an input and an output, said input being connected to said infrared detector, said lamp being positioned to provide an optical path through a cuvette and impinge on said infrared detector, said infrared detector and said preamplifier being constructed and arranged so that the output of the infrared detector and preamplifier will produce an electrical waveform representative of the quantity of $CO_2$ in said cuvette, said waveform having high voltage peaks representing low $CO_2$ and low voltage valleys representing high $CO_2$, said infrared lamp being constructed and arranged to be responsive to the output of said pulse-width modulator and lowpass filter which causes the preamplifier to have a reference (baseline) DC level, a peak detector including
       a first RC network having an input and an output, said first RC network having a predetermined discharge time constant,
       a first switch connected between said preamplifier and said first RC network so that when said first switch is closed the output of said preamplifier will charge said first RC network and when said first switch is open said first RC network will discharge, and
       a first comparator having an output connected to operate said switch and having a first input connected directly to the output of said preamplifier and having a second input connected to the output of said first RC network to compare the voltage level at the output of said preamplifier with the voltage level at the output of said RC network so that said first switch will be opened or closed depending upon the compared voltages, wherein the output from said first RC network will apply a voltage so said pulse-width modulator and said lowpass filter to control the lamp input voltage, a contamination detector including
       a second comparator having an output and two inputs,
       a second RC network having an input connected to the output of said preamplifier and having an output connected to one input of said second comparator, said second RC network having a discharge time constant shorter than said discharge time constant of said first RC network,
       a DC voltage source having a positive terminal and a negative terminal, said negative terminal being connected to a second input of said second comparator and the positive terminal being connected to said second input of said first comparator, the output of said second comparator being connected to operate said first switch to connect the input of said first RC network with the preamplifier output at a preselected value of compared voltages, whereby said contamination detector will override the peak detector and raise the voltage on the lamp in the event of contamination of the cuvette.

2. The $CO_2$ detector as claimed in claim 1, further including a subtractor having a first input coupled to said preamplifier output, and having a second input, a sample-and-hold circuit having an input connectable to said preamplifier output through a second switch and an output connected to said second input of said subtractor, said second switch being constructed and arranged to open and close concurrently with said first switch, whereby the waveform output from said subtractor will produce a waveform representative of the concentration of $CO_2$ in said cuvette, but inverted.

3. The CO₂ detector as claimed in claim 2 further including means for inverting said subtractor output waveform for producing a high quality waveform output.

4. The CO₂ detector as claimed in claim 3 wherein said lamp input voltage is utilizable for triggering an alarm representative of an obstruction in said cuvette.

5. In a CO₂ detector including a cuvette, a circuit including an infrared lamp responsive to a voltage applied to an input thereof, a lamp input circuit, and an infrared detector and detector preamplifier coupled thereto, said preamplifier having an output with a reference (baseline) voltage level, said lamp being positioned to illuminate an optical path through said cuvette so that the infrared detector and detector preamplifier will produce an output signal voltage representative of the quantity of CO₂ in said cuvette, that is, said reference voltage level for minimum CO₂ concentration and a second voltage level for maximum CO₂ concentration, the improvement comprising a feedback gain control loop and an output circuit, said feedback control loop being defined by first means and second means, and said output circuit being defined by third means, said first means comprising a peak detector having a first input connected to said detector preamplifier output so as to be responsive to said output signal voltage, and, a second input connectable to said detector preamplifier output through a first switch, and an output connected to said infrared lamp input circuit, said first means further including a first capacitive timing means including a ground connection and having an input connected to said switch and having an output defining said output of said peak detector, said timing means having a predetermined discharge time constant, whereby said first capacitive timing means is charged by said preamplifier output signal voltage when said first switch is closed and discharges through said ground connection when said first switch is open, and, comparing means having a first input connected to said detector preamplifier output and a second input connected to the output of said first capacitive timing means for comparing said preamplifier output signal voltage and the voltage at the output of said first capacitive timing means, said comparing means having an output constructed and arranged to open and close the first switch in response to the compared voltages so that said first capacitive timing means will discharge when said first switch is open and thus apply its voltage to said lamp input circuit to maintain the reference (baseline) voltage of the detector preamplifier output at a nearly constant value, said second means comprising a contamination detector having an output coupled to operate said first switch, said contamination detector further including a second capacitive timing means having an input charged by said preamplifier output signal voltage, said second capacitive timing means having a shorter discharge time constant than said first capacitive timing means, and further having an output, a second comparing means with one input coupled to the output of said second capacitive timing means and with a second input coupled to the output of said first capacitive timing means for comparing the output voltages of said first and second capacitive timing means, said second comparing means having an output defining said output of the contamination detector which is constructed and arranged to close the first switch in response to compared voltages indicative of blocking of said cuvette, wherein said first capacitive timing means causes said lamp input circuit to drive the lamp with a higher voltage level to maintain the reference voltage level substantially constant;

and said third means including a subtracter having one input coupled to the output of said detector preamplifier so as to be responsive to its output signal voltage, a sample-and-hold circuit having an input coupled to said detector preamplifier through a second switch, said second switch being constructed and arranged so as to be opened and closed simultaneously with said first switch, said sample and hold circuit having an output connected to a second input of said subtracter for eliminating the reference (baseline) voltage in said preamplifier output signal voltage, thereby providing an output signal waveform corresponding to the CO₂ concentration changes occurring within said cuvette and of such quality that the output signal may be useful for diagnostic purposes.

6. The improved detector as claimed in claim 1, wherein said lamp input circuit includes a pulse-width modulator and a lowpass filter between the output of said peak detector and said lamp.

7. The improved detector as claimed in claim 6, wherein said lowpass filter has an output connection utilizable as a contamination warning signal.

* * * * *